United States Patent
Lemke et al.

(10) Patent No.: US 8,161,576 B2
(45) Date of Patent: Apr. 24, 2012

(54) PROTECTIVE HEADGEAR ASSEMBLY

(75) Inventors: Kenneth P. Lemke, Algonquin, IL (US); James A. Piper, St. Charles, IL (US); Mark Edward Miller, Oswego, IL (US); Daniel Ryan Somen, Chicago, IL (US)

(73) Assignee: Sellstrom Manufacturing Company, Palatine, IL (US)

( * ) Notice: Subject to any disclaimer, the term of this patent is extended or adjusted under 35 U.S.C. 154(b) by 593 days.

(21) Appl. No.: 11/670,024

(22) Filed: Feb. 1, 2007

(65) Prior Publication Data

US 2008/0184451 A1    Aug. 7, 2008

(51) Int. Cl.
*A42B 1/22* (2006.01)
*A42B 1/08* (2006.01)
*A42B 1/06* (2006.01)
*A61F 9/06* (2006.01)
*A41D 13/00* (2006.01)

(52) U.S. Cl. .......... 2/418; 2/417; 2/419; 2/420

(58) Field of Classification Search .......... 2/410, 6.2, 2/6.5, 6.7, 6.8, 7, 8.2, 8.3, 8.4, 8.5, 8.7, 8.8, 2/416, 417, 418, 419, 421, 438, 451
See application file for complete search history.

(56) References Cited

U.S. PATENT DOCUMENTS

| | | | | |
|---|---|---|---|---|
| 1,817,475 A | * | 8/1931 | Becker | 224/176 |
| 2,205,742 A | | 6/1940 | Bowers | |
| 2,360,101 A | * | 10/1944 | Bowers | 2/8.1 |
| 2,390,006 A | | 11/1945 | Severy | |
| 2,511,234 A | * | 6/1950 | Anderson | 2/8.1 |
| 2,550,575 A | * | 4/1951 | Malcom | 2/8.1 |
| 2,926,406 A | * | 3/1960 | Edwards et al. | 24/68 B |
| 3,041,622 A | * | 7/1962 | Gurtowski | 2/8.1 |
| 3,047,876 A | * | 8/1962 | Malcom, Jr. | 2/9 |
| 3,090,046 A | * | 5/1963 | Bowers, Sr. | 2/8.1 |
| 3,095,876 A | * | 7/1963 | Meister | 128/206.27 |
| 3,214,768 A | | 11/1965 | Bohner | |
| 3,214,809 A | | 11/1965 | Edwards | |
| 3,325,824 A | * | 6/1967 | Donegan | 2/8.1 |
| 3,444,560 A | | 5/1969 | Northup, Jr. | |
| 3,729,779 A | * | 5/1973 | Porth | 24/68 SK |
| 3,866,244 A | | 2/1975 | Ruck | |
| 4,170,792 A | | 10/1979 | Higgs | |
| 4,479,738 A | | 10/1984 | Kubnick | |
| 4,718,127 A | | 1/1988 | Rittmann et al. | |
| 4,807,305 A | | 2/1989 | Sundahl | |
| 4,888,831 A | | 12/1989 | Oleson | |

(Continued)

OTHER PUBLICATIONS

PCT International Search Report, International Application No. PCT/US07/80289, Apr. 14, 2008.

*Primary Examiner* — Gary L Welch
*Assistant Examiner* — Jane Yoon
(74) *Attorney, Agent, or Firm* — Vedder Price PC

(57) ABSTRACT

The present invention generally relates to protective headgear worn by a user to protect his eyes, head, and face. More particularly, the present invention is directed to a protective headgear assembly used by welders and the like wherein a headgear strap can be tightened or loosened upon the ratcheting of a knob connected to the headgear strap. The headgear strap can also be automatically disengaged for removal of the headgear by pulling the knob away from the user's head.

15 Claims, 18 Drawing Sheets

U.S. PATENT DOCUMENTS

| | | | |
|---|---|---|---|
| 4,907,299 A | 3/1990 | Arai | |
| 4,920,585 A | 5/1990 | Arai | |
| 5,091,997 A | 3/1992 | Foehl | |
| 5,177,817 A | 1/1993 | Kamata | |
| 5,182,816 A | 2/1993 | Arai | |
| 5,185,889 A | 2/1993 | Kamata | |
| 5,333,329 A | 8/1994 | Hong | |
| 5,357,654 A * | 10/1994 | Hsing-Chi | 24/68 B |
| 5,373,588 A | 12/1994 | Hede et al. | |
| 5,571,217 A * | 11/1996 | Del Bon et al. | 2/9 |
| 5,647,060 A | 7/1997 | Lee | |
| 5,987,651 A | 11/1999 | Tanaka | |
| 6,256,798 B1 * | 7/2001 | Egolf et al. | 2/421 |
| 6,260,197 B1 | 7/2001 | Hoogewind | |
| 6,260,213 B1 | 7/2001 | Eom et al. | |
| 6,264,392 B1 | 7/2001 | Wise et al. | |
| 6,301,721 B1 | 10/2001 | Arai | |
| 6,622,313 B1 | 9/2003 | Choi et al. | |
| 6,622,314 B1 | 9/2003 | Kim et al. | |
| 6,654,969 B2 | 12/2003 | Taniuchi | |
| 6,708,376 B1 * | 3/2004 | Landry | 24/68 R |
| 6,732,380 B1 | 5/2004 | Lee | |
| 6,807,679 B1 | 10/2004 | Wang-Lee | |
| 7,000,262 B2 | 2/2006 | Bielefeld | |
| 7,007,306 B2 | 3/2006 | Howard et al. | |
| 7,043,772 B2 * | 5/2006 | Bielefeld et al. | 2/418 |
| 7,089,603 B2 * | 8/2006 | Ketterer et al. | 2/418 |
| 7,174,575 B1 * | 2/2007 | Scherer | 2/418 |
| 7,565,704 B2 * | 7/2009 | Wu | 2/418 |
| 8,037,548 B2 * | 10/2011 | Alexander et al. | 2/418 |
| 2001/0039671 A1 | 11/2001 | Robinson et al. | |
| 2003/0074722 A1 | 4/2003 | Lee | |
| 2005/0071909 A1 | 4/2005 | Diaz et al. | |
| 2005/0262619 A1 * | 12/2005 | Musal et al. | 2/421 |
| 2005/0267518 A1 * | 12/2005 | Wright et al. | 606/203 |
| 2006/0048285 A1 | 3/2006 | Bielefeld et al. | |
| 2006/0080761 A1 * | 4/2006 | Huh | 2/424 |
| 2008/0109947 A1 * | 5/2008 | Dubois | 2/414 |

* cited by examiner

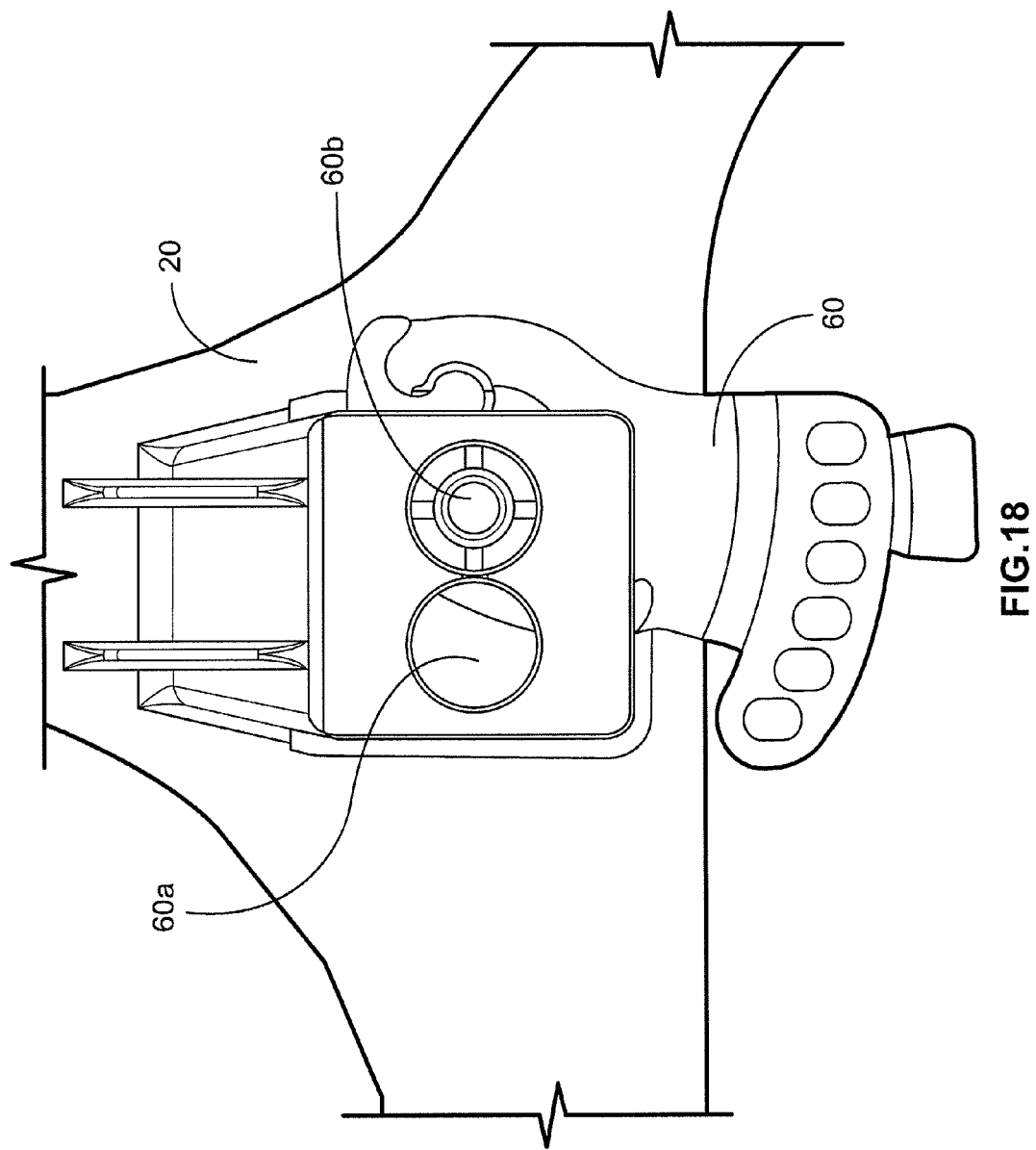

PROTECTIVE HEADGEAR ASSEMBLY

FIELD OF THE INVENTION

The present invention generally relates to protective headgear worn by a user to protect his eyes, head, and face. More particularly, the present invention is directed to a protective headgear assembly used by welders wherein a headgear strap can be tightened or loosened upon the ratcheting of a knob connected to the headgear strap. The headgear strap can also be automatically loosened for removal of the headgear by pulling the knob away from the user's head.

BACKGROUND OF THE INVENTION

It has become commonplace for protective headgear to be worn while a user is undertaking a number of different activities. Frequently, there are safety-related laws or standards that require certain types of protective headgear to be worn, depending on the occupation or activity a user performs. Different types of protective headgear are generally known in the art. Certain activities, such as welding, require the wearing of protective headgear, i.e., a welding helmet, to protect the user's head, neck, face, and eyes. Other examples of protective headgear include bicycle helmets, motorcycle helmets, or helmets used during sporting activities.

Protective headgear used for different purposes can differ greatly in their design. Generally though, protective headgear will include: (1) a protective body, i.e., a helmet, to cover the user's head, (2) a type of headgear strap attached to the helmet to enable the headgear to remain on the user's head during use, and (3) a suspension system to separate the user's head from the helmet. Specifically with regard to welding, the user must also protect his eyes from dangerous sparks, heat, infrared and ultraviolet rays emitted when welding, while still remaining able to see in front of him. Accordingly, the protective headgear worn while welding further includes a face portion that acts to shield a user's face while allowing the user to see through the face portion to view his work. In addition, protective headgear worn while welding should enable the user to pivot the helmet portion of the headgear while the suspension system and headgear strap remain on the user's head.

The headgear strap is typically adjustable to enable the user to change the length of the strap to conform to the circumference of the user's head. An adjustable headgear strap allows the protective headgear to fit comfortably and securely during use, which is imperative during dangerous practices such as welding. The strap can be of closed loop formation, or utilize a type of ratchet mechanism that enables the length of the strap to be adjusted manually.

While ratchet mechanisms are generally known in the art and allow a user to manually loosen or tighten the headgear strap, none utilize a single mechanism that can allow for both adjustment of the size and fit of the headgear strap, and the ability to disengage the entire mechanism for automatic loosening of the headgear strap so that the protective headgear can be pulled off the user's head. Without a single quick-release mechanism, it can often be awkward and take needless time to ratchet the mechanism to loosen the headgear strap. Moreover, in the event of a need to remove the protective headgear quickly, such as in the event of an accident or other emergency, users, such as welders, should have a simple mechanism to free themselves of the oftentimes heavy and restrictive headgear.

There is a need to provide a protective headgear assembly with a headgear strap that can be easily adjusted for length to enable a user to be able to wear the protective headgear assembly securely.

There is also a need for a protective headgear assembly that can be removed in a simple, quick and efficient manner.

There is also a need for a protective headgear assembly wherein the helmet can pivot from a closed position (during use) to an open position (when not in use) while the headgear strap and suspension system remain in place on the user's head.

Accordingly, it is desirable to provide a protective headgear assembly wherein the headgear strap can be both adjusted for length and disengaged utilizing a single mechanism. By use of a single mechanism, a user can perform both actions in an easy and straightforward way.

It is also desirable to provide a protective headgear assembly wherein the helmet is capable of pivoting from a closed position (during use) to an open position (when not in use) while the headgear strap and suspension system remain in place on the user's head.

Thus, it is an object of the present invention to provide a protective headgear assembly which effectively addresses the aforementioned shortcomings associated with prior apparatuses of this general type, as well as to provide the above-mentioned desirable features.

SUMMARY OF THE INVENTION

The purpose and advantages of the present invention will be set forth in and apparent from the description that follows, as well as will be learned by practice of the invention. Additional advantages of the invention will be realized and attained by methods and systems particularly pointed out in the written description and claims thereof, as well as from the appended drawings.

The present invention is generally embodied in a protective headgear assembly. The protective headgear assembly may be utilized for any application wherein a user desires to protect his eyes, head and face. In particular, the present invention is directed to a protective headgear assembly used to protect a user's eyes, head and face during work procedures. For example, the protective headgear assembly can be used by welders to protect the welders' eyes, head and face during welding procedures.

In accordance with one embodiment of the present invention, the protective headgear assembly comprises a protective body, a headgear strap, and a quick-release ratchet mechanism. In the preferred embodiment, the protective body is a helmet. It will be appreciated that the protective body can also be a face shield.

The quick-release mechanism of the present invention comprises a gear system and an adjusting knob. The headgear strap fits around the circumference of a user's head in order to retain the protective headgear apparatus securely on the user's head. The quick-release mechanism is attached to the headgear strap and allows the user to: (1) manually adjust the length of the headgear strap, and (2) disengage the gear system in order for the user to automatically loosen the headgear strap and quickly take the protective headgear assembly off of his head. Specifically, the knob can be ratcheted clockwise or counterclockwise to adjust the length of the headgear strap to ensure a secure fit on the user's head. Turning the adjusting knob clockwise tightens the headgear strap and locks it to a selected size. Turning the knob counterclockwise loosens the headgear strap. In order for the user to disengage the gear system to unlock the selected size and allow for immediate headgear removal, the knob can be pulled away from the user's head. The same pulling action away from the user's head also can loosen the headgear strap to a selected size.

In another embodiment of the present invention, the protective headgear assembly further comprises an attaching assembly. In this embodiment, the helmet is attached to the headgear strap by means of attaching assemblies well known in the art, such as, e.g., as described in U.S. Pat. No. 4,479,738, the entire contents of which is hereby incorporated by reference herein.

In another embodiment of the present invention, the helmet can be attached to the headgear strap by means of a side-pivot device. The side-pivot device allows for the helmet to pivot from a closed position (during use) to an open position (when not in use) while the headgear strap remains in place on the operator's head. The side-pivot device limits the range of motion through which the helmet can pivot and also provides a positive dented stop at either end of the pivot path. The positive dented stops allow the helmet to rest in an open or closed position until adjusted by the user. The side-pivot device is distinctively a single piece that interacts with both the headgear strap and a pivot post that holds the device, strap and helmet together. It eliminates the need for a separate locking bolt. In addition, the headgear strap is able to accommodate the pivot device in two different positions. The positions move the helmet closer or farther from the front of the operator's head. The functionality of the pivot remains the same in either position.

In yet another embodiment of the present invention, the helmet can be attached to the headgear strap by means of a multi-position stop construction on a first side of the helmet and a detent cap construction on a second side of the helmet. In this embodiment, a five-position stop pivots with the helmet. The five-position stop limits travel of the helmet in both directions as it interacts with the headgear strap. The closed position (during use) of the helmet is determined by the interaction between the five-position stop and a pin located on the helmet. In the detent cap construction of this embodiment of the present invention, a washer key and detent cap interact and lock together to keep the helmet locked in an open (not in use) position. The washer key and detent cap are unlocked when the helmet is in the closed position.

It is to be understood that both the foregoing general description and the following detailed description are exemplary and provided for purposes of explanation only, and are not restrictive of the invention, as claimed. Further features and objects of the present invention will become more fully apparent in the following description of the preferred embodiments and from the appended claims.

The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

In describing the preferred embodiments, reference is made to the accompanying drawing figures wherein like parts have like reference numerals, and wherein:

FIG. 18 is a perspective view of the side-pivot device of FIG. 13 utilizing the back mounting hole of the headgear strap.

It should be understood that the present invention is not limited to the preferred embodiments illustrated.

DETAILED DESCRIPTION OF THE INVENTION

Referring generally to FIGS. 1-18, and upon review of this description, it will be appreciated that the apparatus of the present invention generally may be embodied within numerous configurations.

Figure 1:
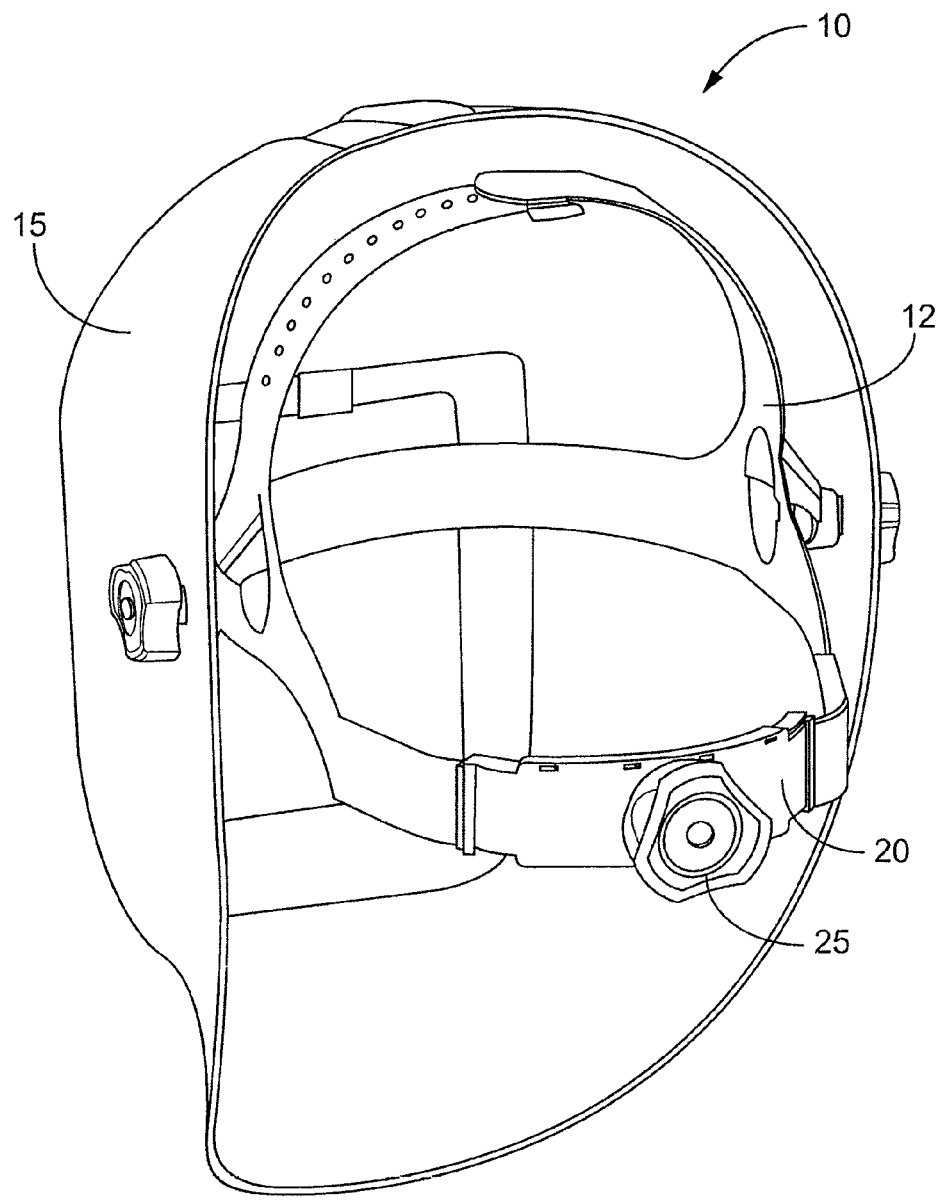
FIG. 1 is a perspective view of the protective headgear assembly during use in accordance with the present invention.

FIG. 1 is a perspective view of the protective headgear assembly 10 during use on a user's head. As shown in the preferred embodiment, the protective headgear assembly 10 generally includes: a helmet 15 to protect the user's head and eyes; a suspension system 12 to separate the user's head from the helmet; a headgear strap 20; and a quick-release mechanism 25. It will be appreciated that the helmet 15 can be any type of protective body that protects a user's head and eyes, including, e.g., a face shield. It will also be appreciated that the helmet 15 of the protective headgear assembly 10 can be made of any hard material that resists impact. For example, among other hard materials, the helmet 15 can be made of metal, plastic, or resin fiber. The headgear strap 20 extends around the circumference of the user's head and provides for a secure and comfortable fit depending on the user's manual adjustments. The quick-release mechanism 25 preferably is integral to the headgear strap 20 and lies at the back of the user's head during use.

Figure 2:
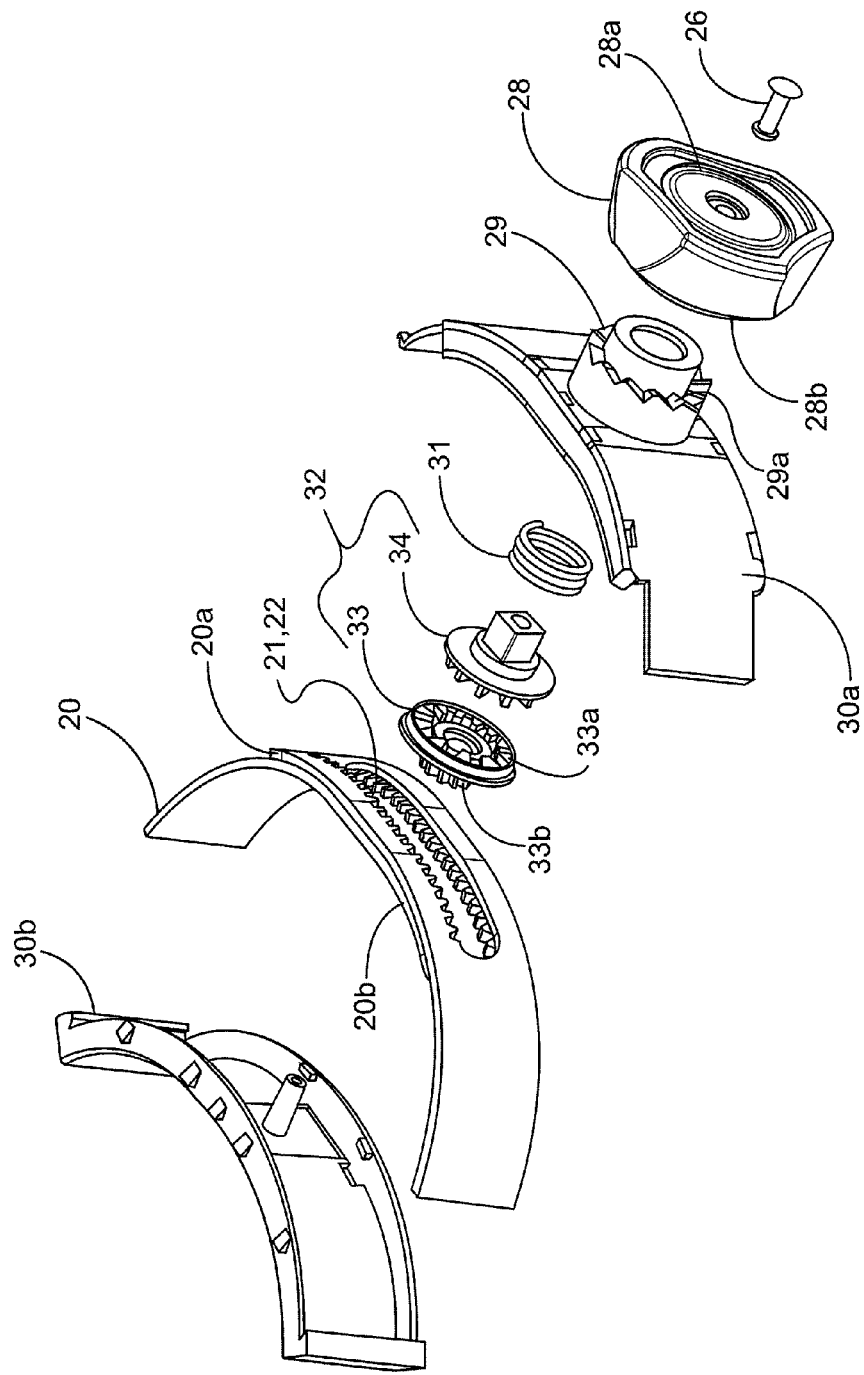
FIG. 2 is an exploded perspective view of a quick-release mechanism made in accordance with the present invention.
Figure 3:
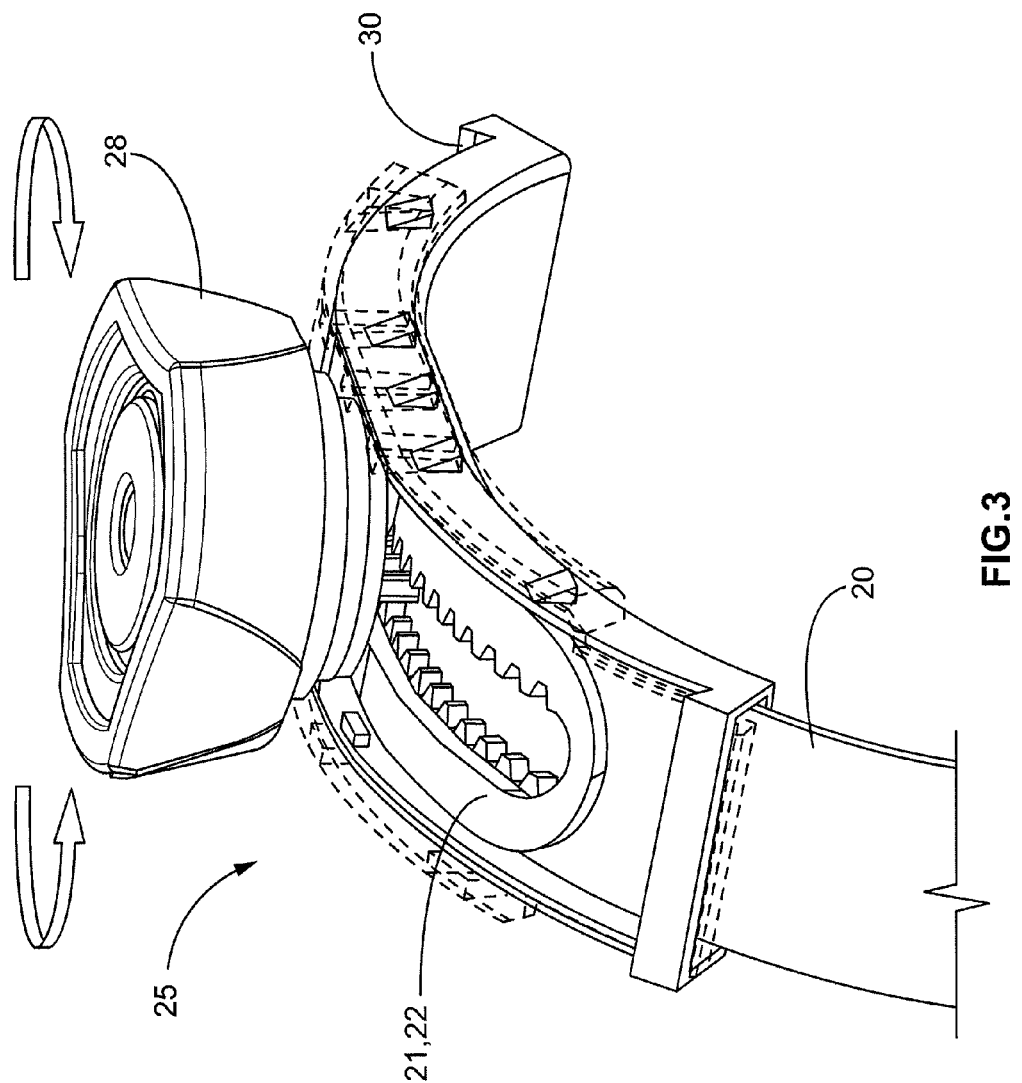
FIG. 3 is a perspective view of the quick-release mechanism of FIG. 2.

Referring now to a preferred embodiment illustrated in FIGS. 2 and 3, the quick-release mechanism 25 comprises: (1) an adjusting knob 28 that enables a user to adjust the length of the headgear strap 20; (2) a housing 30 to define an internal cavity for receiving the headgear strap 20; and (3) a gear system 32 for manipulation of the length of the headgear strap 20. In this exemplary embodiment, the adjusting knob 28 has a first end 28a and a second end 28b. The first end 28a provides a component that the user can manipulate to adjust the length of the headgear strap 20. The second end 28b includes a cylindrical opening that receives a cylindrical covering 29 of the gear system 32. The cylindrical covering 29 is positioned on the exterior side of an outer housing section 30a. The second end 28b also comprises ratchet teeth (not shown) that engage ratchet teeth 29a of the cylindrical covering 29. The outer housing section 30a and an inner housing section 30b join to form the housing 30, as shown in FIG. 3, and collectively define the internal cavity for receiving the headgear strap 20. It will be appreciated that the housing 30 can be arc-shaped to fit securely around the user's head. The quick-release mechanism 25 is preferably held together by means of a river pin 26 that enters through the first end 28a of the adjusting knob 28. The pin 26 holds the knob 28 adjacent to a lock gear 34 with a spring 31 interspersed between.

In the preferred embodiment, as illustrated in FIG. 2, the gear system 32 of the quick-release mechanism 25 is comprised of a drive gear 33 and the lock gear 34. The drive gear 33 comprises two integral sides 33a and 33b. A first side 33a of the drive gear 33 preferably has radially inward projecting teeth which cooperate with radially outward projecting teeth of the lock gear 34. A second side 33b of the drive gear 33 preferably is a cog that engages two overlapping ends 20a and 20b of the headgear strap 20. The first end 20a and second end 20b of the headgear strap each include lateral slots 21, 22 that have gripping teeth formed along the periphery of each slot. The quick-release mechanism 25 further preferably comprises the spring 31 positioned within the cylindrical covering 29 which abuts a flange disposed on the cylindrical covering 29 on one end, and the lock gear 34 at the other end. The spring 31 biases the lock gear 34 into engagement with the inward projecting teeth of the first side 33a of the drive gear 33.

Figure 4:
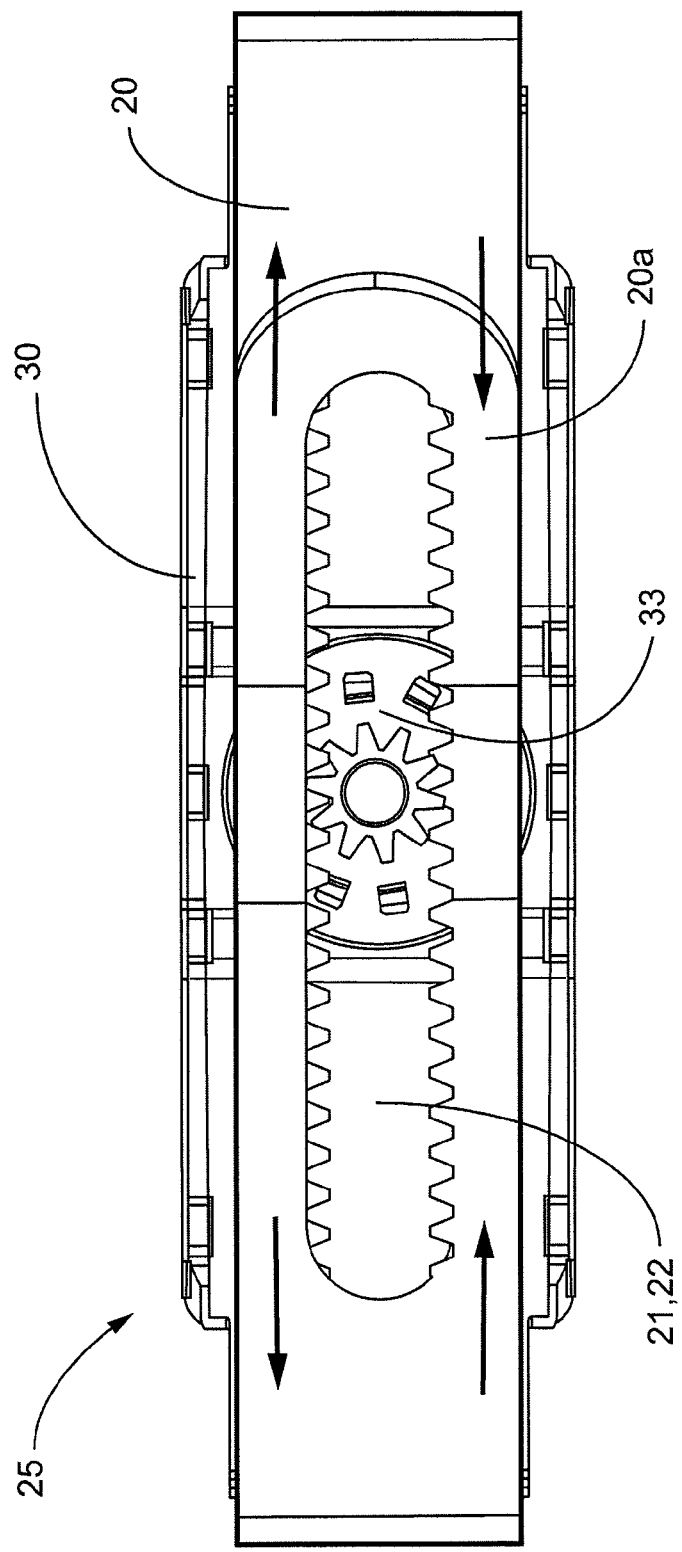
FIG. 4 is a detailed view of the quick-release mechanism of FIG. 2, illustrating lateral movement of the overlapping ends of the headgear strap caused by rotation of the adjusting knob.
Figure 5:
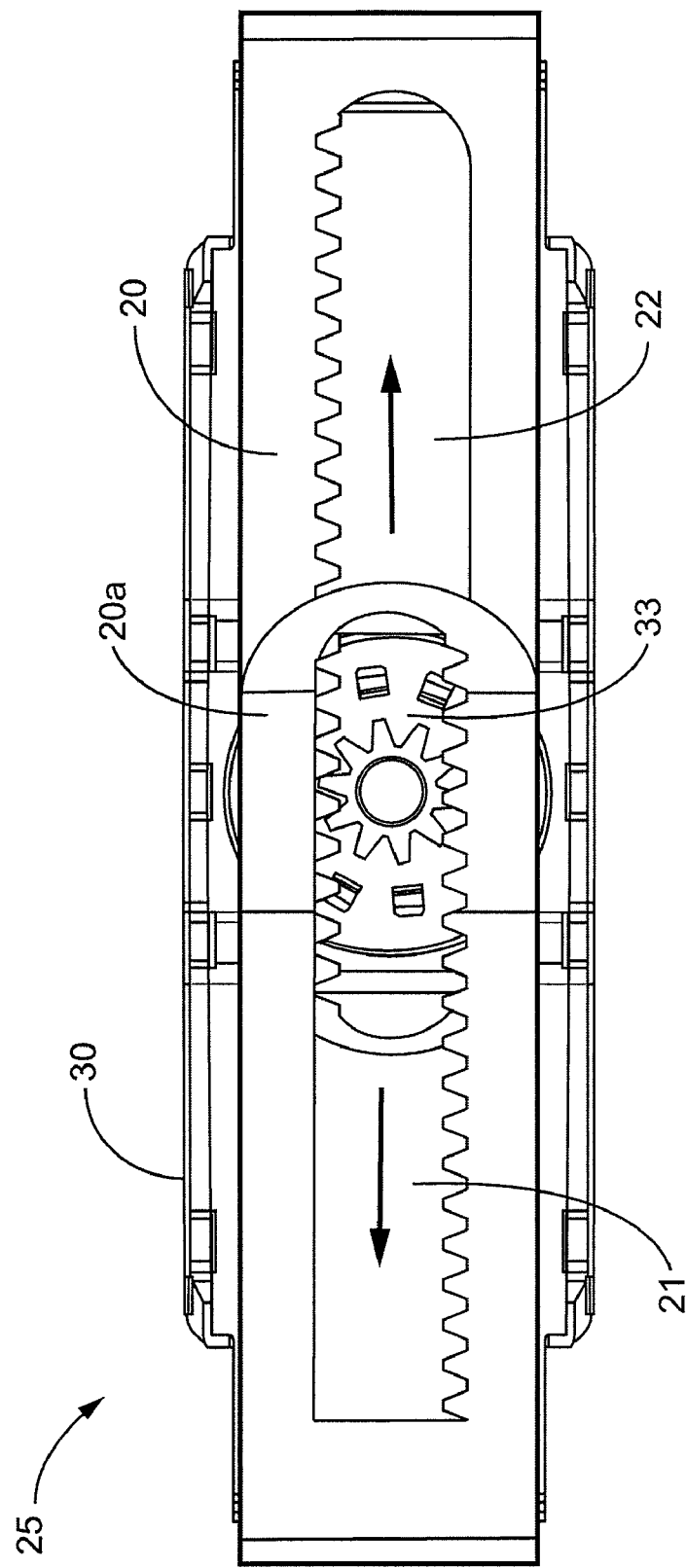
FIG. 5 is a detailed view of the quick-release mechanism of FIG. 2, illustrating movement of the overlapping ends caused by counterclockwise rotation of the adjusting knob.

The ratchet teeth 29a of the cylindrical covering 29 engaged with the ratchet teeth of the second side of the adjusting knob 28b restrict movement of the adjusting knob 28 by means of the spring 31. The lock gear 34 is rigidly connected to the adjusting knob 28. Accordingly, manual turning of the adjusting knob 28 by a user (see FIG. 3) causes the gear system 32 to turn and engage the gripping teeth of the two lateral slots 21, 22 of the headgear strap 20, as shown in FIG. 4. Specifically, when the user turns the adjusting knob 28 clockwise, the first overlapping end 20a and the second overlapping end 20b of the headgear strap 20 move toward one another laterally to decrease the circumference of the headgear strap 20. Similarly, as shown in FIG. 5, when the user turns the adjusting knob 28 counterclockwise, the first overlapping end 20a and the second overlapping end 20b move away from one another laterally to increase the circumference of the headgear strap 20. The user must overcome sufficient torque provided by the spring 31 on the adjusting knob 28 in order to once again change the selected size of the headgear strap 20. The gripping teeth of the two lateral slots 21, 22 of the headgear strap 20 allow for incremental tightening of the headgear strap 20. The user is accordingly able to adjust the headgear strap 20 so as to have a secure fit around his head. Once the user stops turning the adjusting knob 28 in either direction, the ratchet teeth 29a of the cylindrical covering 29 engaged with the ratchet teeth of the second side of the adjusting knob 28b prevents lateral movement of the overlapping ends 20a, 20b of the headgear strap 20 and therefore locks the headgear strap 20 into a selected size and fit around the user's head.

Figure 6:
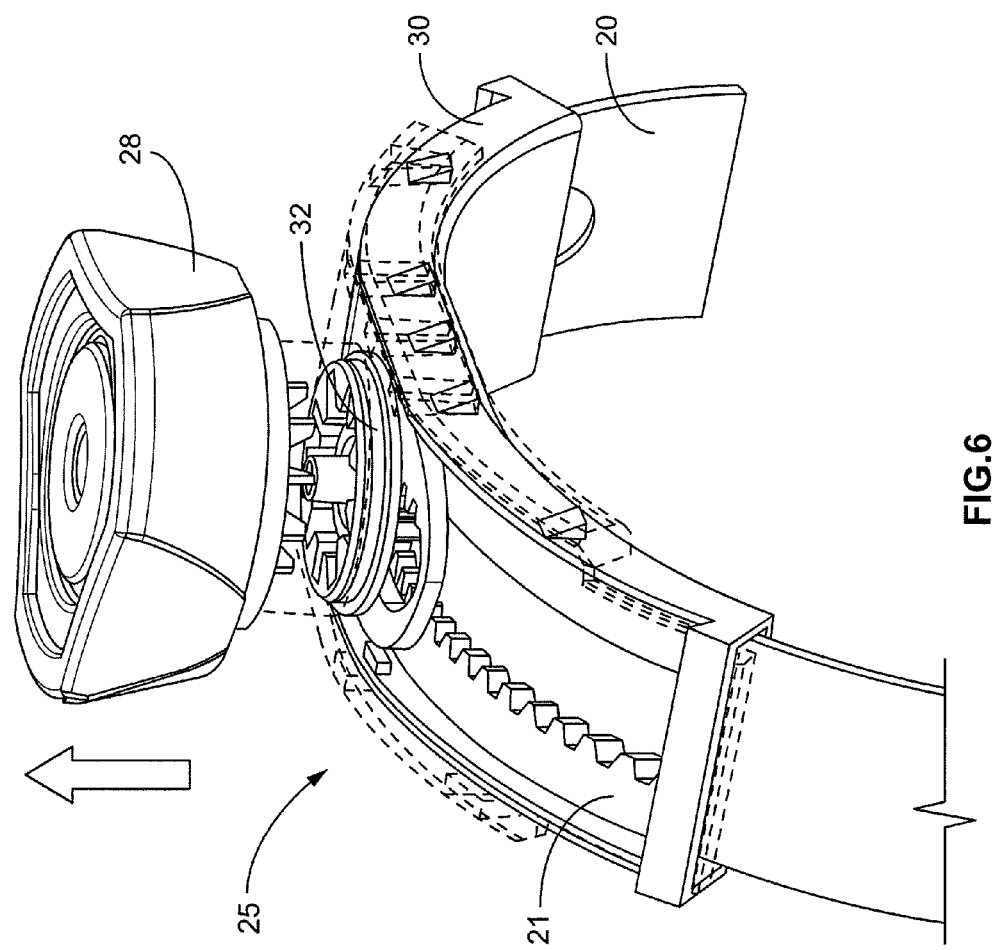
FIG. 6 is a perspective view of the quick-release mechanism of FIG. 2, illustrating movement of the adjusting knob and disengagement of the gear system caused by the pulling of the adjusting knob.
Figure 7:
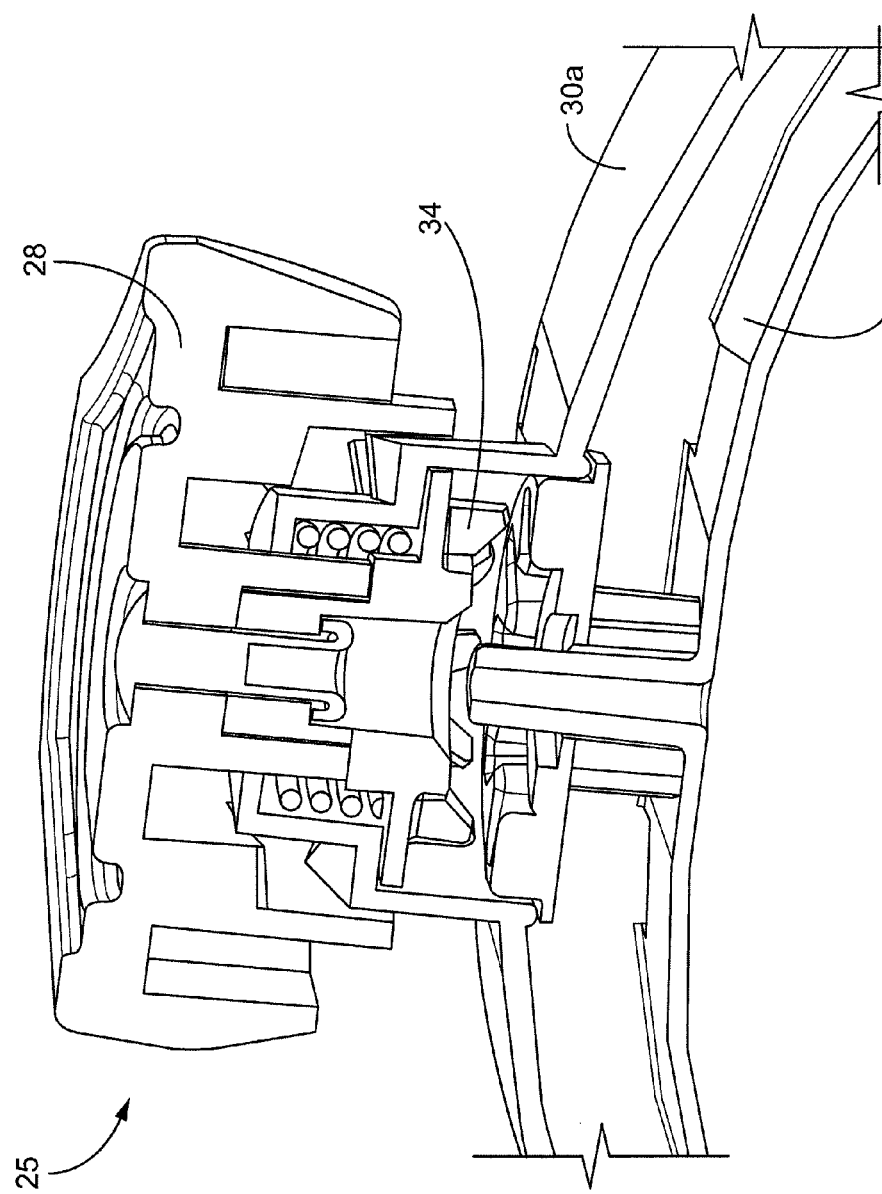
FIG. 7 is a cut-away perspective view of the adjusting knob of the quick-release mechanism of FIG. 2 when the adjusting knob is pulled, illustrating the disengagement of the gear system.

Referring now to a preferred embodiment in FIGS. 6 and 7, the adjusting knob 28 of the quick-release mechanism 25 can further be manually pulled in a direction away from the housing 30 to disengage the gear system 32. When a user pulls the adjusting knob 28 in a direction away from the user's head, the lock gear 34 is forced to separate from the drive gear 33, causing the drive gear 33 to be able to freely rotate and unlock the headgear strap 20 from the selected size. As a result, the first overlapping end 20a and the second overlapping end 20b of the headgear strap 20 are able to move away from one another without any ratcheting of the adjusting knob 28. The user can simply pull the protective headgear assembly 10 off of his head.

Figure 8:
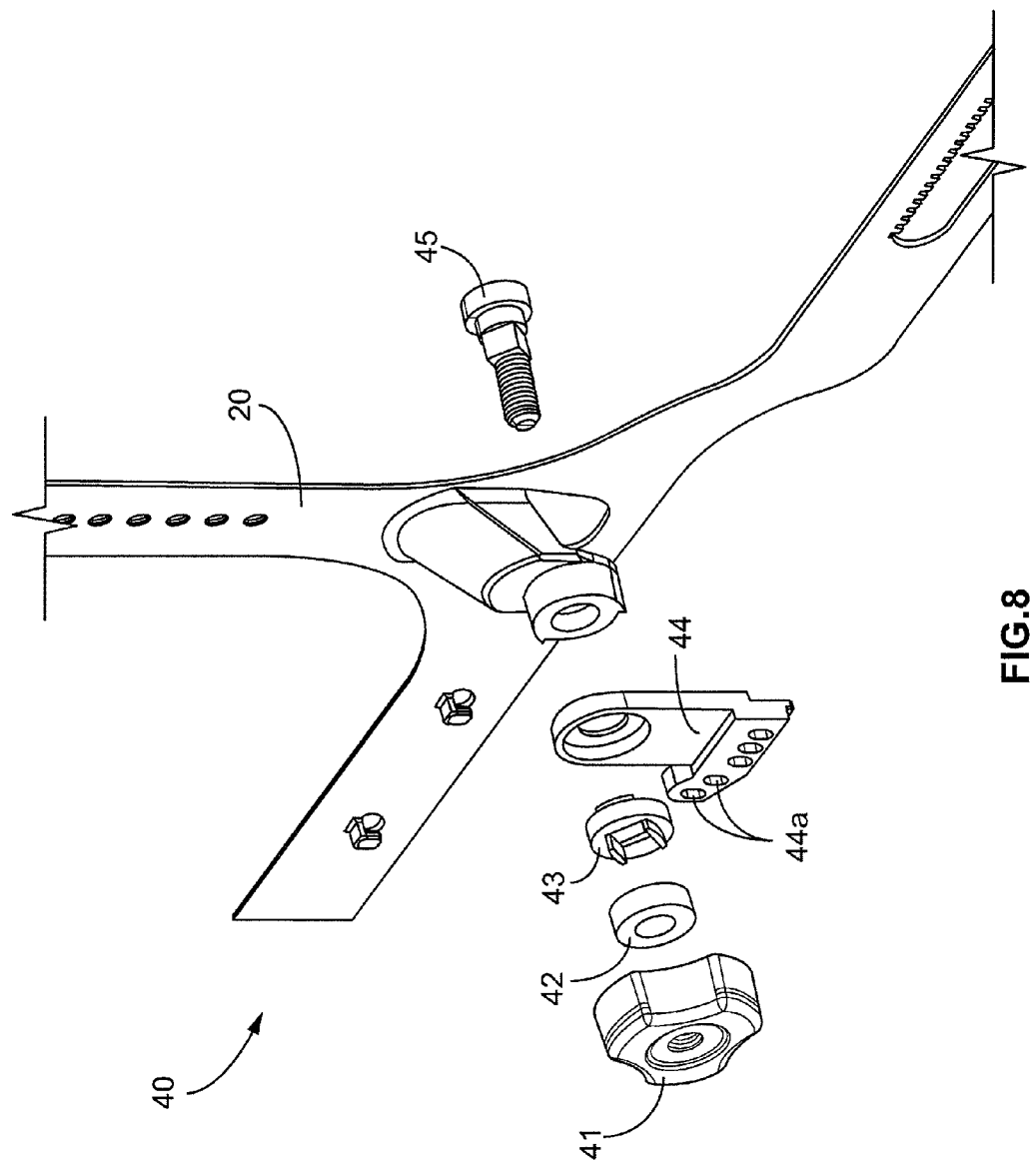
FIG. 8 is an exploded perspective view of the multi-position stop construction made in accordance with the present invention.
Figure 9:
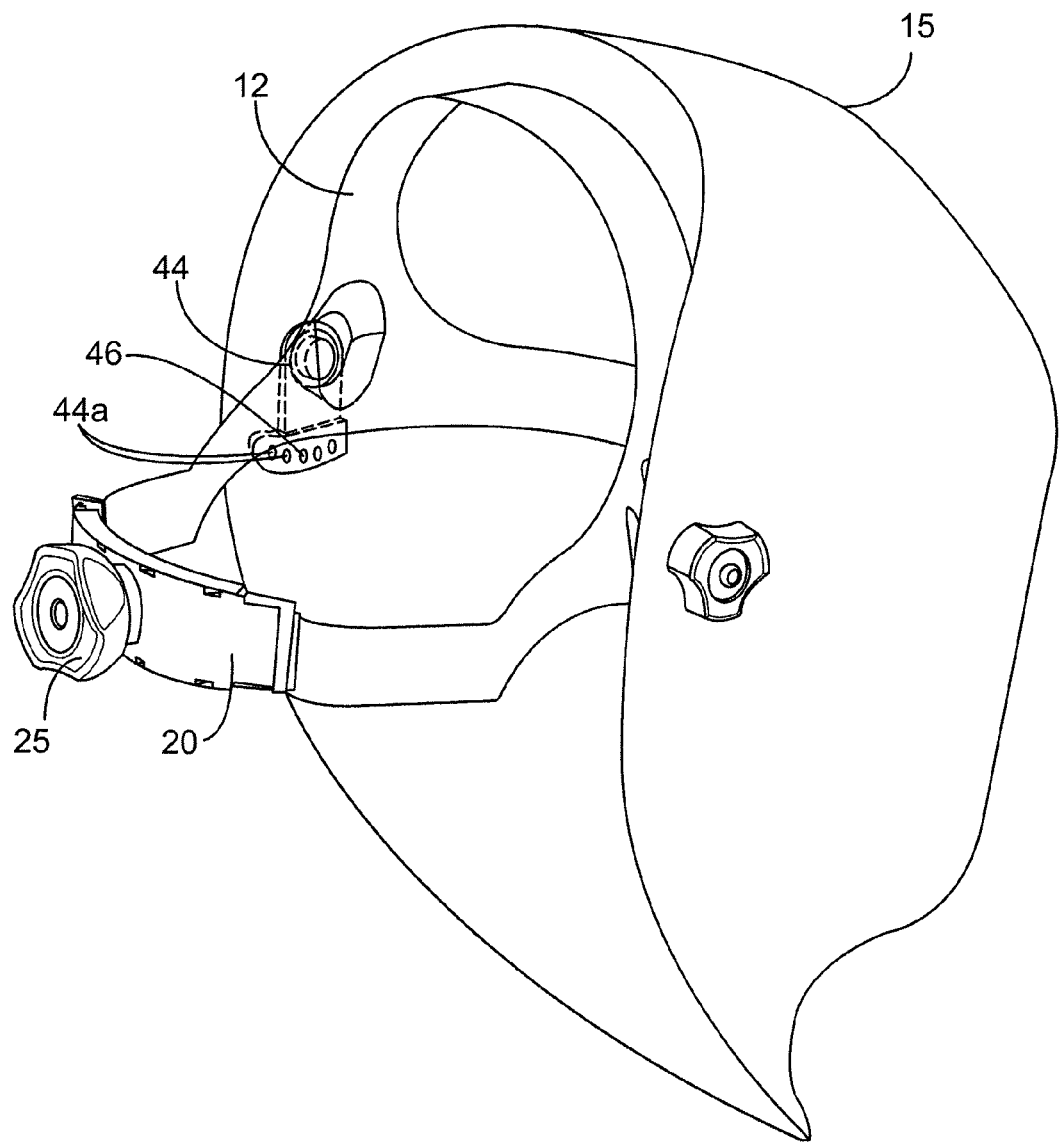
FIG. 9 is a perspective view of the protective headgear assembly illustrating the five-position stop engaged with the pin affixed to the helmet.

It will be appreciated that various attachment means can be employed to affix the headgear strap 20 to the helmet 15. Referring now to a preferred embodiment in FIGS. 8-10, the protective headgear assembly 10 comprises a multi-position stop construction 40 on a first side of the helmet 15, and a detent cap construction 50 on a second side of the helmet 15. As shown in FIGS. 8 and 9, the multi-position stop construction 40 comprises a knob 41, a washer 42, a washer key 43, and a five-position stop 44, all connected to the headgear strap 20 by means of a pivot post 45. The five-pivot stop 44 comprises five adjustment holes 44a and pivots with the helmet 15. It will be appreciated that any number of adjustment holes 44a can be used in accordance with the present invention. The adjustment holes 44a determine the position of the helmet 15 with respect to the suspension system 12 and headgear strap 20. A pin 46 is affixed to the helmet in order to receive an adjustment hole 44a. The helmet 15 can be positioned closer or farther from the face of the user depending on the placement of the pin 46 into an adjustment hole 44a.

Figure 10:
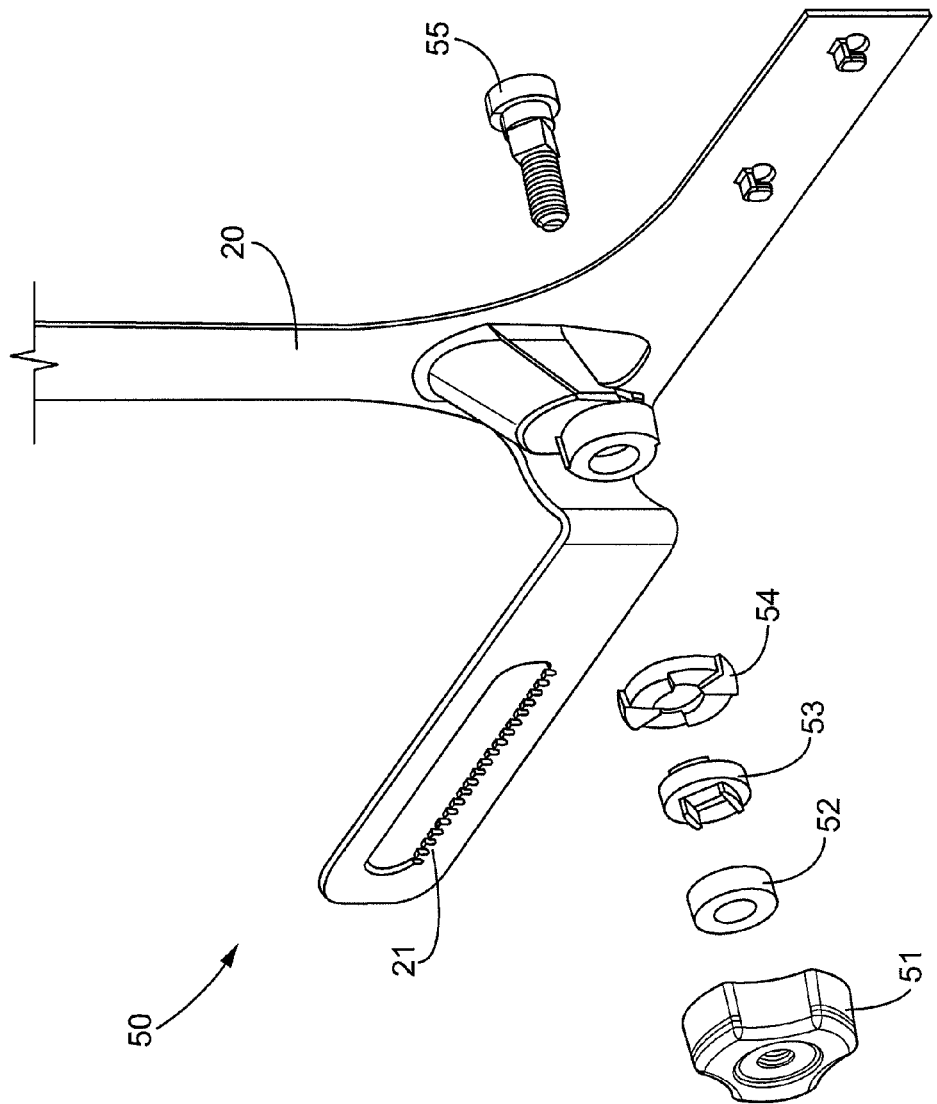
FIG. 10 is an exploded perspective view of a detent cap construction made in accordance with the present invention.
Figure 11:
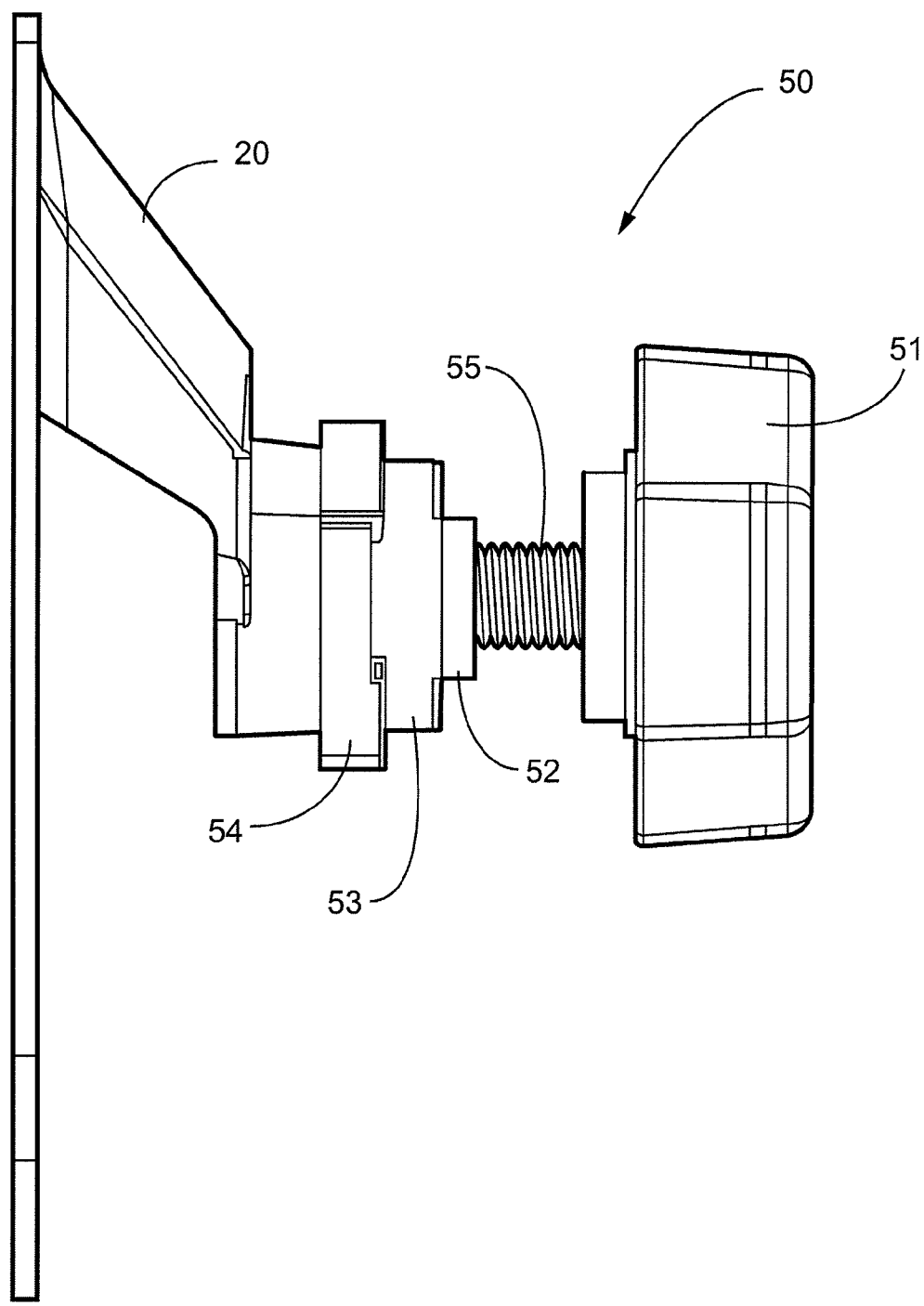
FIG. 11 is a perspective view of the detent cap construction of FIG. 10, illustrating the washer key and the detent cap in a locked position.
Figure 12:
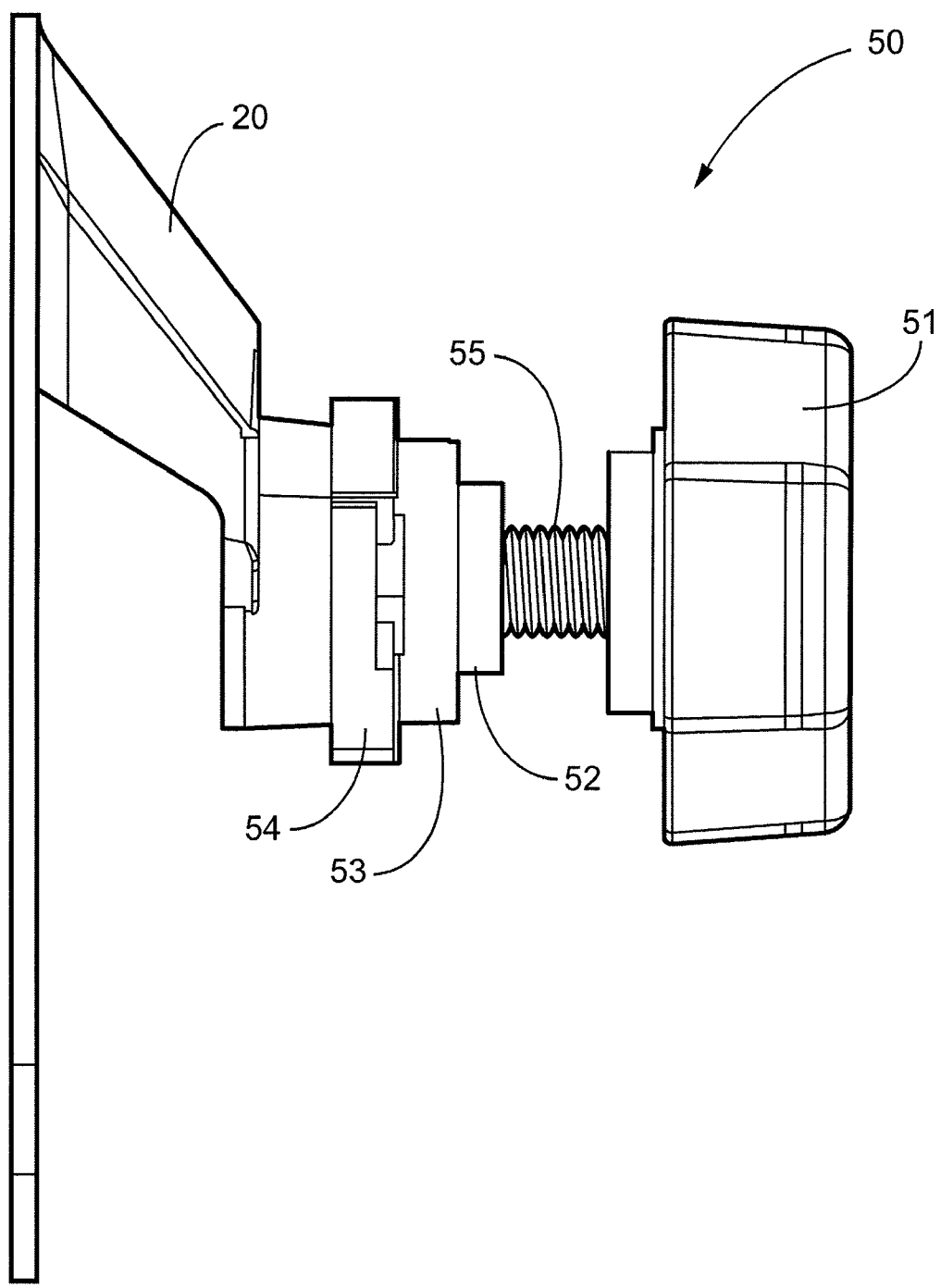
FIG. 12 is a perspective view of detent cap construction of FIG. 10, illustrating the washer key and the detent cap in an unlocked position.
Figure 13:
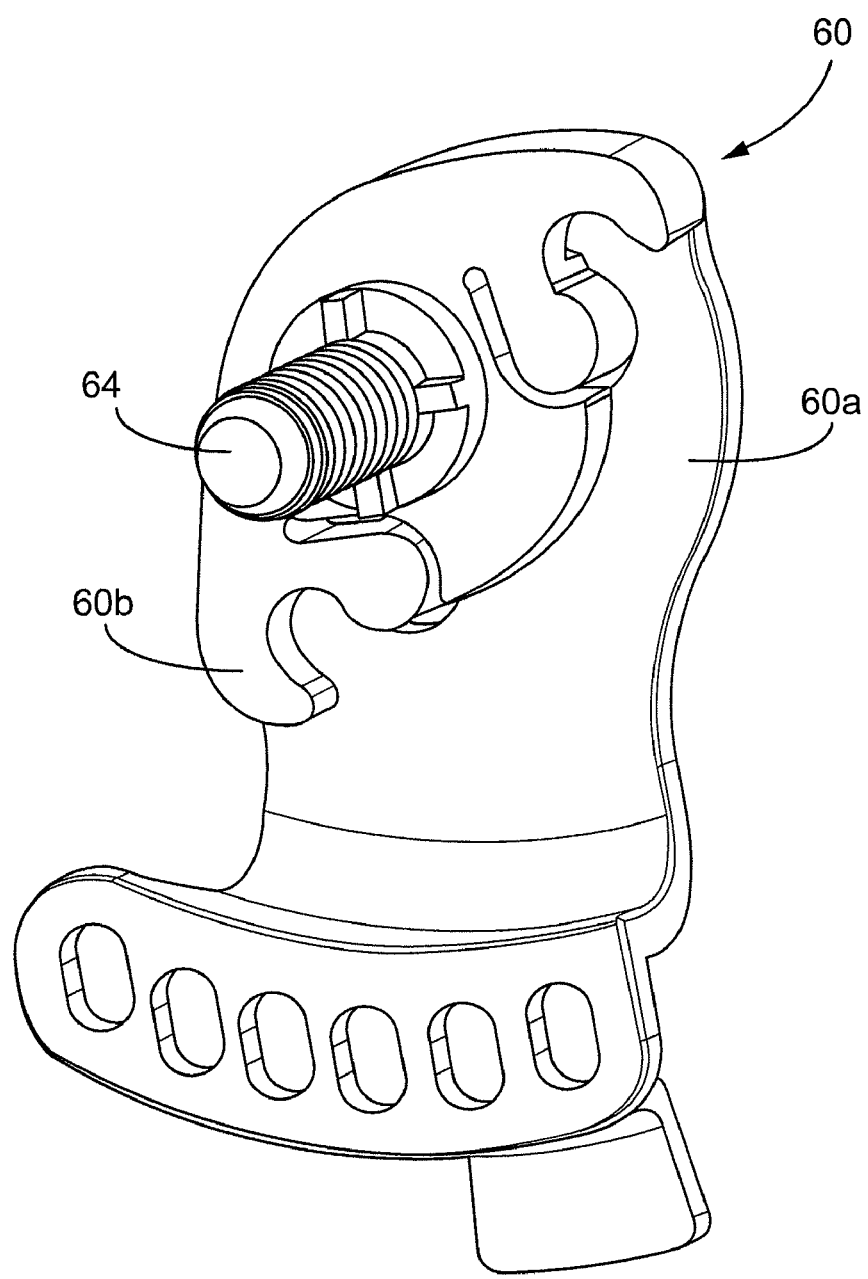
FIG. 13 is an enlarged view of a side-pivot device made in accordance with the present invention.
Figure 14:
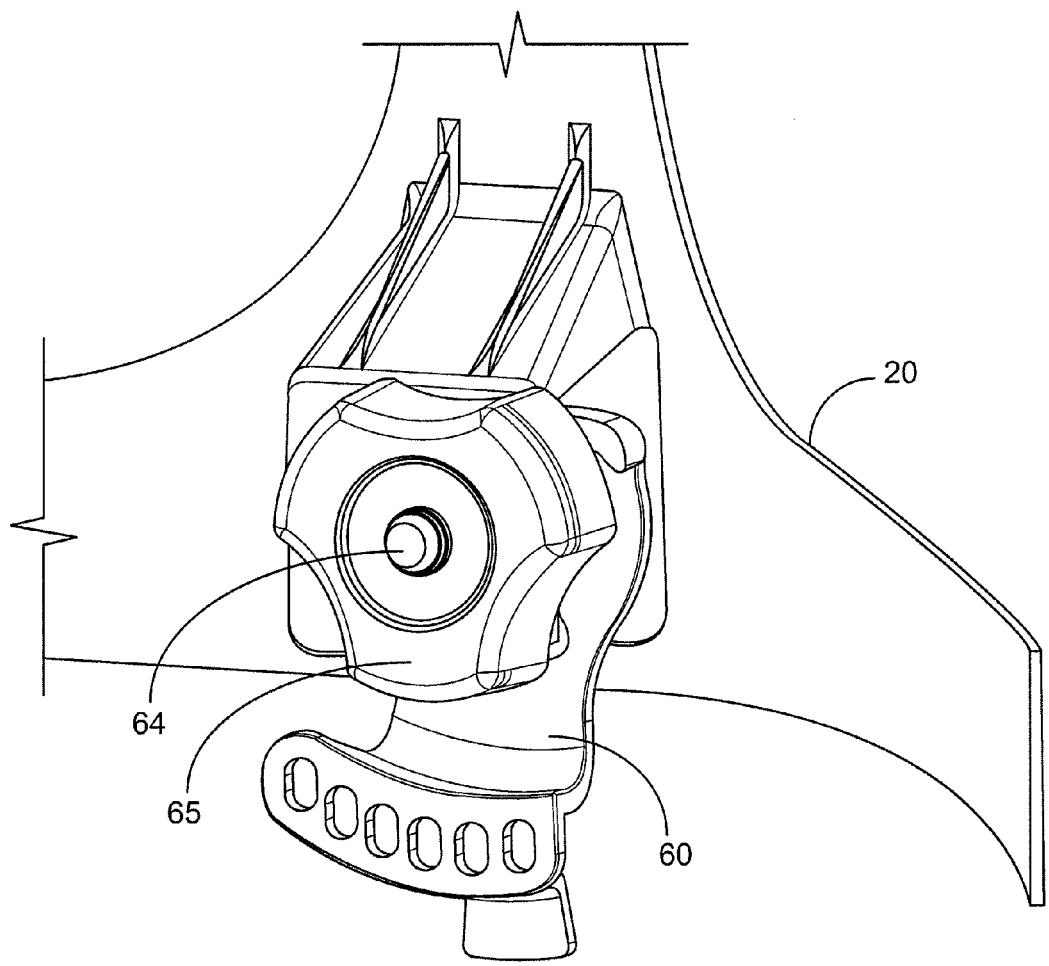
FIG. 14 is a perspective view of the side-pivot device of FIG. 13 connected to the headgear strap of the present invention.

As shown in FIG. 10, the detent cap construction 50 on the second side of the helmet 15 comprises a knob 51, a washer 52, a washer key 53, and a detent cap 54, all connected to the headgear strap 20 by means of a pivot post 55. The detent cap 54 is preferably comprised of at least one notch that matches and interacts with at least one notch on the washer key 53. The washer key 53 and the detent cap 54 rotate relative to each other. In order to lock the helmet 15 into an open position, the user lifts the helmet 15 until the washer key 53 and the detent cap 54 lock together, as shown in FIG. 11. The user must overcome the force necessary to unlock the washer key 53 and the detent cap 54 by pulling the helmet 15 down into a closed position, see FIG. 12.

Figure 15:
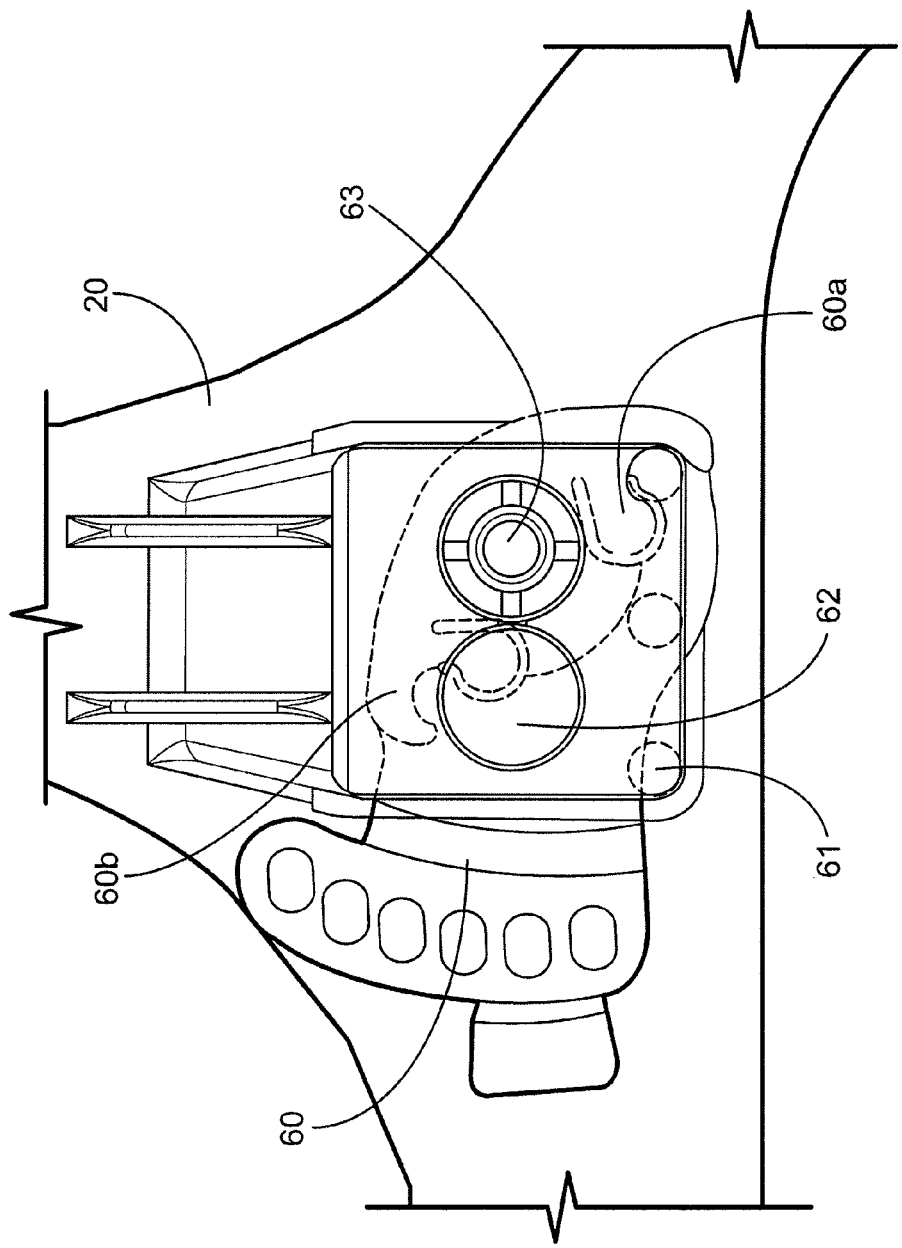
FIG. 15 is a detailed view of the side-pivot device of FIG. 13 in an open (not in use) position.
Figure 16:
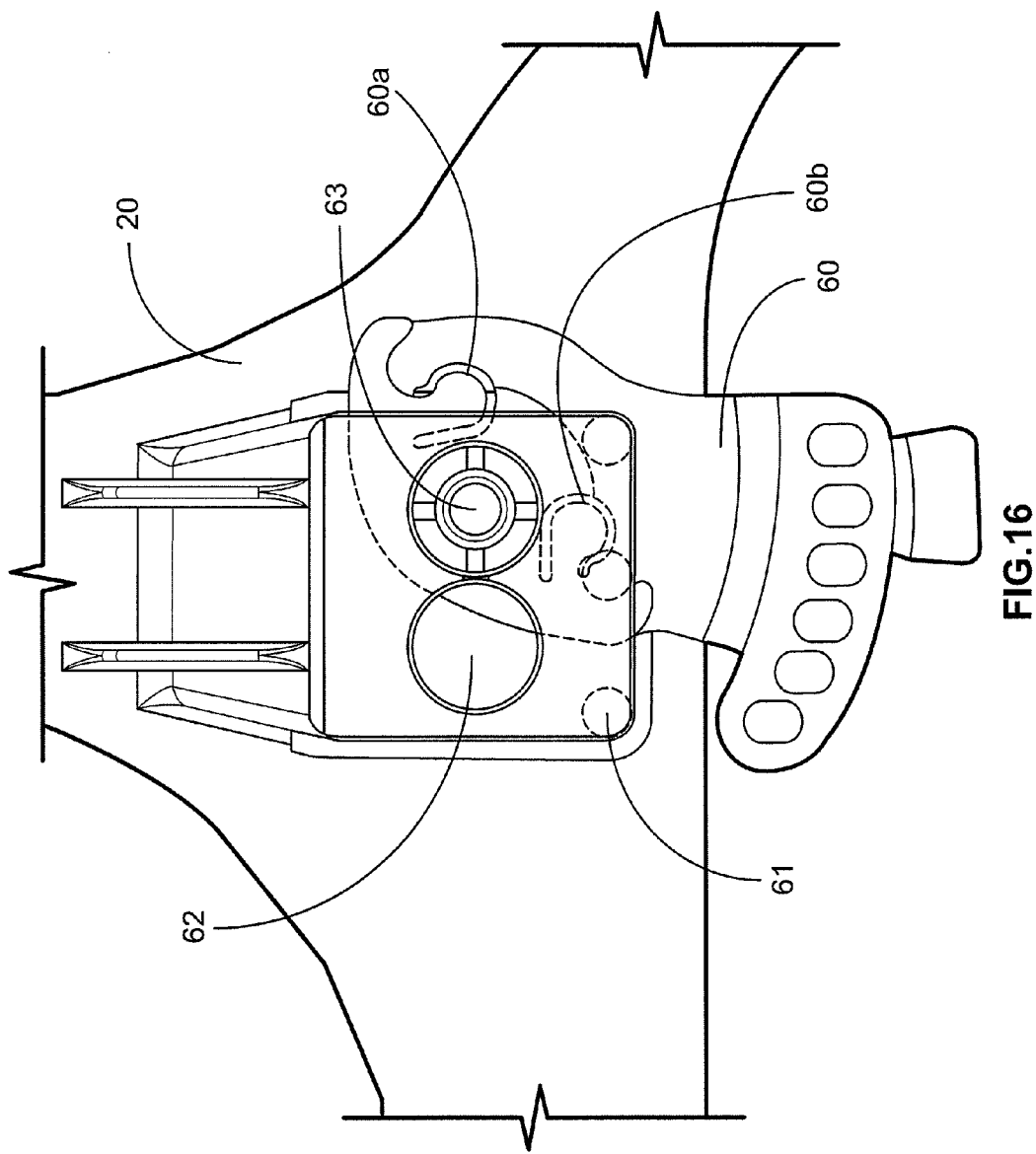
FIG. 16 is a detailed view of the side-pivot device of FIG. 13 in a closed (during use) position.
Figure 17:
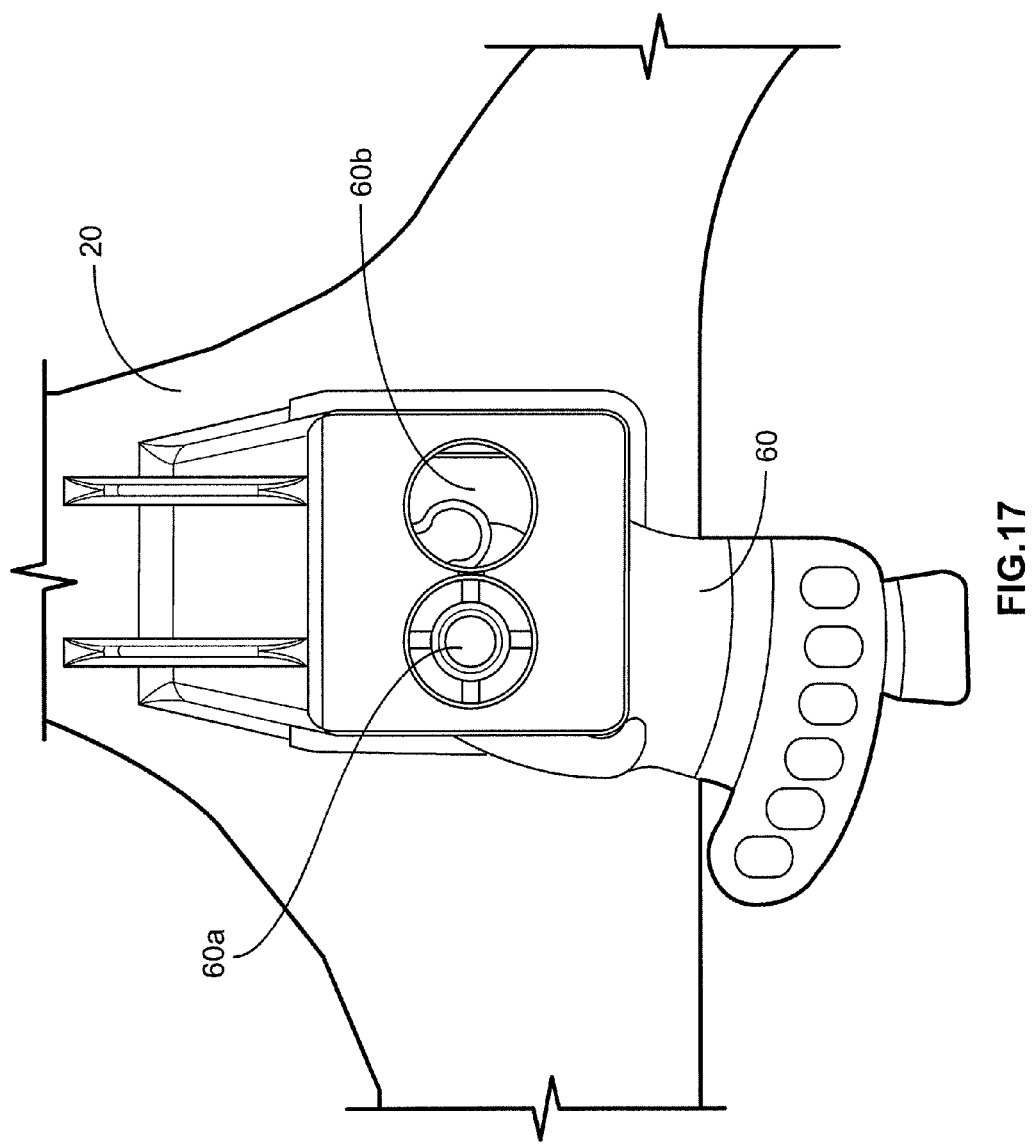
FIG. 17 is a perspective view of the side-pivot device of FIG. 13 utilizing the front mounting hole of the headgear strap.

Referring now to an alternative embodiment illustrated in FIGS. 13-18, it will be appreciated that the helmet 15 of the present invention can also be attached to the headgear strap 20 by means of a side-pivot device 60, a pivot post 64, and a knob 65. As shown in FIGS. 15 and 16, the side-pivot device 60 comprises a pair of spring arms 60a, 60b that interact with a series of pins 61 on the headgear strap 20 to provide a dented stop at either end of the pivot path. The spring arms 60a, 60b restrain the helmet 15 in either an open (not in use) position (see FIG. 15), or a closed (in use) position (see FIG. 16) until adjusted by the user. Further, as shown in FIGS. 17 and 18, in this alternative embodiment, the headgear strap 20 can accommodate the side-pivot device 60 in two different positions by means of a pair of mounting holes 62, 63. The mounting holes 62, 63 are provided on the headgear strap 20 so that the helmet 15 may be selectively positioned closer or farther from the front of the user's face. For example, FIG. 17 illustrates the side-pivot device 60 attached to the headgear strap 20 by means of the pivot post 64 received through the front mounting hole 62 of the headgear strap 20, thereby positioning the helmet 15 farther in front of the operator's head than if the side-pivot device 60 was affixed to the back mounting hole 63 (see FIG. 18). The functionality of the side-pivot device 60 remains the same in either position.

It should be appreciated that merely preferred embodiments of the invention have been described above. However, many modifications and variations to the preferred embodiments will be apparent to those skilled in the art, which will be within the spirit and scope of the invention. Therefore, the invention should not be limited to the described embodiments. To ascertain the full scope of the invention, the following claims should be referenced.

What is claimed is:

1. A protective headgear assembly comprising:
   a protective body;
   a headgear strap having first and second ends, said headgear strap connected to said protective body; and
   a quick-release mechanism comprising a housing for receiving said first and second ends of said headgear strap, an adjustment assembly including a knob and gear system, said gear system including a drive gear in engagement with said first and second ends and a lock gear moveable between a first position in engagement with said drive gear and a second position disengaged from said drive gear, said knob fixedly connected to said lock gear and rotatable in a first direction to lengthen said headgear strap and an opposition direction to shorten said headgear strap when said lock gear is in said first position, said knob is moveable outwardly from said first and second ends, moving said lock gear to said second position thereby allowing free movement of said first and second ends of said headgear strap without rotation of said knob.

2. A headgear assembly as defined in claim 1, wherein the quick release mechanism prevents lateral movement of the first and second ends of the headgear strap when said lock gear is in said first position.

3. A headgear assembly as defined in claim 1, wherein the knob of the quick-release mechanism is manually rotatable about an axis normal to said first and second ends.

4. An assembly as defined in claim 1, wherein the protective body is a helmet.

5. An assembly as defined in claim 1, wherein the protective body is a face shield.

6. A protective headgear assembly comprising:
   a protective body having a first side and a second side;
   a headgear strap having first and second ends, said headgear strap connected to said first side of said protective body;
   a quick-release mechanism comprising a housing for receiving said first and second ends of said headgear strap, an adjustment assembly including a knob and gear system, said gear system including a drive gear in engagement with said first and second ends and a lock gear moveable between a first position in engagement with said drive gear and a second position disengaged from said drive gear, said knob fixedly connected to said lock gear and rotatable in a first direction to lengthen said headgear strap and an opposition direction to shorten said headgear strap when said lock gear is in said first position, said knob is moveable outwardly from said first and second ends moving said lock gear to said second position allowing free movement of said first and second ends of said headgear strap without rotation of said knob;
   a multi-position stop construction on said first side of said helmet; and
   a detent cap construction on said second side of said helmet.

7. An assembly as defined in claim 6, wherein the multi-position stop construction comprises:
   a handle;
   a washer;
   a washer key; and
   a five-position stop;
   wherein the multi-position stop construction is attached to the headgear strap by means of a pivot post.

8. An assembly as defined in claim 7, wherein the five-position stop comprises at least one adjustment hole.

9. An assembly as defined in claim 8, wherein the detent cap construction comprises:
   a handle;
   a washer;
   a washer key; and
   a detent cap,
   wherein the detent cap construction is attached to the headgear strap by means of a pivot post.

10. An assembly as defined in claim 9, wherein the detent cap comprises at least one notch that engages the washer key in order to lock the helmet into an open position.

11. An assembly as defined in claim 9, wherein the detent cap comprises at least one notch that engages the washer key in order to lock the helmet into a closed position.

12. A headgear assembly as defined in claim 6, wherein the quick release mechanism prevents lateral movement of the first and second ends of the headgear strap when said lock gear is in said first position.

13. A headgear assembly as defined in claim 6, wherein the knob of the quick-release mechanism is manually rotatable about an axis normal to said first and second ends.

14. An assembly as defined in claim 6, wherein the protective body is a helmet.

15. An assembly as defined in claim 6, wherein the protective body is a face shield.

* * * * *